United States Patent
Gongaware et al.

(10) Patent No.: US 12,113,931 B2
(45) Date of Patent: Oct. 8, 2024

(54) METHOD OF PRE-VERIFYING PHONE NUMBERS FOR CALL ATTESTATION

(71) Applicant: Doximity, Inc., San Francisco, CA (US)

(72) Inventors: Zachary Gongaware, Stanwood, WA (US); Christopher Frame, Culver City, CA (US); Jude Capachietti, Haleiwa, HI (US)

(73) Assignee: Doximity, Inc., San Francisco, CA (US)

( * ) Notice: Subject to any disclaimer, the term of this patent is extended or adjusted under 35 U.S.C. 154(b) by 157 days.

(21) Appl. No.: 17/741,325

(22) Filed: May 10, 2022

(65) Prior Publication Data
US 2023/0370544 A1   Nov. 16, 2023

(51) Int. Cl.
*H04M 3/42*      (2006.01)
*H04M 3/436*     (2006.01)
*H04M 3/51*      (2006.01)

(52) U.S. Cl.
CPC ..... *H04M 3/42042* (2013.01); *H04M 3/4365* (2013.01); *H04M 3/51* (2013.01)

(58) Field of Classification Search
CPC ... H04M 3/42042; H04M 3/4365; H04M 3/51
USPC ........................................................ 455/415
See application file for complete search history.

(56) References Cited

U.S. PATENT DOCUMENTS

| | | | | |
|---|---|---|---|---|
| 10,462,080 B1* | 10/2019 | Jones | ..................... | G06F 16/906 |
| 2014/0274002 A1* | 9/2014 | Hogan | ..................... | G06F 16/00 |
| | | | | 455/415 |
| 2021/0337384 A1* | 10/2021 | Synal | .................. | H04W 12/069 |

OTHER PUBLICATIONS

"3rd Generation Partnership Project; Technical Specification Group Services and Systems Aspects; Study on IMS Enhanced Spoofed Call Prevention and Detection (Release 13)", 3GPP TR 33.832 vo.3.0 (Aug. 2015), Technical Report, Valbonne, France, © 2014, 3GPP Organizational Partners (Aug. 2015), pp. 1-15.
ATIS-1000074.v002, "Signature-based Handling of Asserted information using toKENS (Shaken)", ATIS & SIP Forum Joint Standard, © 2021 by Alliance for Telecommunications Industry Solutions and by SIP Forum LLC (Jul. 12, 2021), 21 pages.
PCT International Search Report and Written Opinion from related PCT Application No. PCT/US2023/020669 mailed on Jul. 25, 2023, 12 pages.

* cited by examiner

*Primary Examiner* — Ahmad F. Matar
*Assistant Examiner* — Jirapon Tulop
(74) *Attorney, Agent, or Firm* — Womble Bond Dickinson (US) LLP

(57) ABSTRACT

A system and method of determining pre-verification information for use by a certification authority to verify and attest phone numbers associated with healthcare facilities is provided. The method includes receiving an unverified phone number and determining, using one or more matching operations, whether the unverified phone number is associated with a healthcare facility. In response to such determination, the unverified phone number and a facility name associated with the healthcare facility is sent to a certification authority server to be used to verify the unverified phone number. Other embodiments are described and claimed.

20 Claims, 6 Drawing Sheets

METHOD OF PRE-VERIFYING PHONE NUMBERS FOR CALL ATTESTATION

TECHNICAL FIELD

This disclosure generally relates to phone calls. In particular, this disclosure relates to pre-verifying phone numbers for assigning an attestation rating to a phone call.

BACKGROUND

Healthcare providers (e.g., doctors, nurses, etc.) may provide various health related services and products to patients. Patients may often visit health care facilities (e.g., hospitals, clinics, etc.) to receive the health related services and products. For example, a patient may visit a clinic or a hospital for a checkup or to speak with a doctor about a particular medical/health issue. Healthcare providers may also speak with patients on phone calls.

BRIEF DESCRIPTION OF THE DRAWINGS

Embodiments and implementations of the present disclosure will be understood more fully from the detailed description given below and from the accompanying drawings of various aspects and implementations of the disclosure, which, however, should not be taken to limit the disclosure to the specific embodiments or implementations, but are for explanation and understanding only.

DETAILED DESCRIPTION

Figure 1:
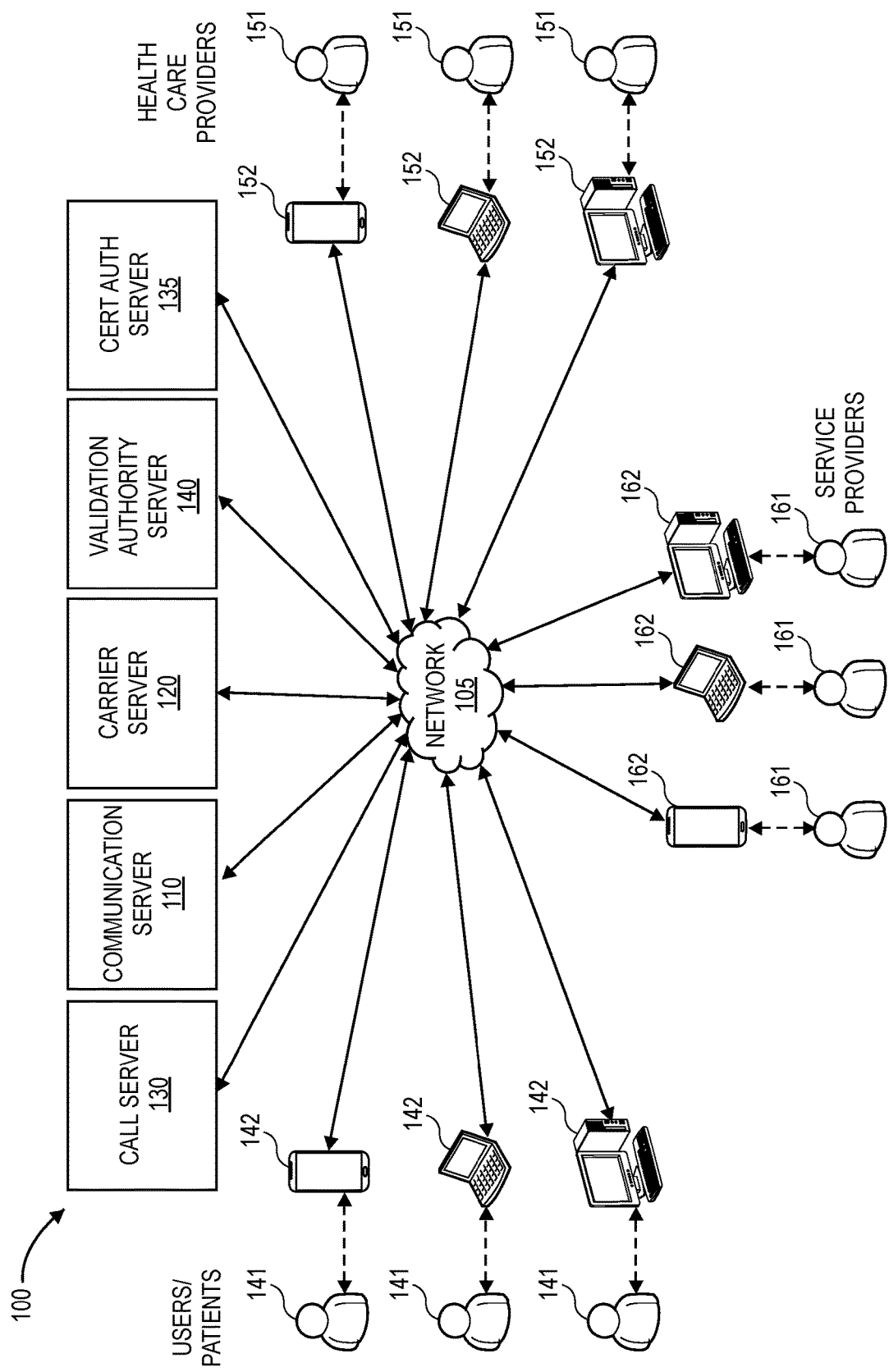
FIG. 1 is a diagram illustrating an example network architecture in accordance with one or more embodiments of the disclosure.

As discussed above, a healthcare professional, e.g., a doctor, may call a patient to provide health-related services. The doctor may place the call from a personal mobile device, however, the doctor may prefer that the patient see the phone number of the incoming call as that of the healthcare facility whom the doctor represents for that health-related service, rather than from the doctor's personal mobile device. As described below, such legitimate phone number substitution may be used to cause the patient to see the incoming call as coming from the healthcare facility, even when the call is placed from the personal mobile device.

Secure Telephony Identify Revisited/Secure Handling of Asserted Information Using Tokens (STIR/SHAKEN) are technology standards that use certificates to digitally sign phone calls. The signed phone calls verify caller identity. When the doctor places a phone call to a patient using a substituted phone number from a personal mobile device, carriers of the doctor and/or patient can attest that the doctor is a legitimate caller, e.g., not a spam caller, and connect the phone call to allow the doctor and the patient to converse. More particularly, carriers can attach an attestation rating to the call to designate a trustworthiness of the call information. Call services can attest a call request by using a rating system of "A," "B," or "C." As described below, an "A" attestation is the highest quality rating, which designates higher trustworthiness, and a "C" rating is the lowest quality rating, which designates lower trustworthiness. Without a sufficient attestation rating, the patient may see the incoming call as potential spam and not answer or, potentially, the originating or terminating carrier could automatically prevent the call from being placed. In either case, the doctor will not be able to reach the patient through the phone call to provide valuable health-related services. A method of pre-verifying phone numbers, such as the legitimately substituted phone number used by the physician, would facilitate attestation of such phone calls to ensure that the patient efficiently receives healthcare from the doctor.

In some instances, a doctor may initiate a phone call through a communication service that does not own a phone number being legitimately substituted, e.g., a phone number of the healthcare facility. Without certifying a right to use the phone number, the communication service may send a call request to a call service, however, the call service may only attest the phone call with a "B" attestation rating. That is, the call service may originate the call with partial attestation indicating that the caller's identity is known, but the right of the communication service to use the calling number has not been verified. In effect, this may be used to indicate the phone call as potentially a spam call, and the terminating carrier or the patient may block or avoid the phone call. To obtain an "A" attestation rating by the call service, the communication service can self-sign the phone call with a digital certificate supplied by a certification authority. The certification authority can provide the digital certificate to the communication service. To supply the digital certificate for self-signing, however, the certification authority may require pre-verification information that associates the phone number with a known healthcare facility. As such, a method can include the communication service receiving and pre-verifying the phone number, and then sending the pre-verification information to the certification authority for use in verifying the phone number for attestation. The pre-verification can include determining whether the unverified phone number is associated with a healthcare facility. Additional details of the method, and systems configured to perform the method, are described below.

FIG. 1 is a diagram illustrating an example network architecture, in accordance with one or more embodiments of the disclosure. A network architecture 100 includes a network 105, a carrier server 120, a call server 130, a certification authority server 135, users 141, computing devices 142, healthcare providers 151, computing devices 152, service providers 161, and computing devices 162.

In one embodiment, the users 141 may be patients who use services and/or products provided by one or more of the healthcare providers 151 or service providers 161. Each user 141 may use a computing device 142 to communicate with one or more of a healthcare provider 151 and/or a service provider 161. Examples of computing devices 142 may include, but are not limited to, a mobile device, e.g., a smartphone, a tablet computer, or a laptop computer, or a desktop computer, etc.

In one embodiment, the healthcare providers 151 may be people who provide health related services and/or products to the user. Examples of healthcare providers 151 may include, but are not limited to, doctors, pharmacists, dentists, nurses, therapists, psychologists, technicians, surgeons, etc. Each healthcare provider 151 may use a computing device 152 (e.g., smartphone, tablet computer, etc.) to communicate with one or more of the users 141 or the service providers 161. Communications between the healthcare provider 151 and the user 141 may be one-directional communications. For example, the healthcare provider 151 can initiate a call to a user 141 such that the computing device 142 receives a call having a substituted phone number. If the user 141 calls this number back, they may be connected to, e.g., a facility having the phone number that was substituted, rather than computer device 152 that initiated the call.

In one embodiment, a service provider 161 may provide additional or ancillary services to one or more of the users 141 or the healthcare providers 151. Examples of service providers 151 may include, but are not limited to, interpreters (e.g., a language interpreter), insurance providers, billing specialists, etc. Each service provider 161 may use a computing device 162 (e.g., smartphone, tablet computer, etc.) to communicate with one or more of the users 141 or the healthcare providers 151. Communications may be initiated by the healthcare provider 151, e.g., by calling them to initiate a call or to add them to an active call as additional participants.

As discussed above, a healthcare provider 151 (e.g., a doctor) may communicate with a user (e.g., a patient) via a phone call. The system architecture 100 may allow a healthcare provider 151 to place the phone call to the user 141 through one or more of the communication server 110, the call server 130, or the carrier server 120.

In one embodiment, the communication server 110 may connect with one or more of the networked devices to facilitate call requests that will connect the patients 142 or service providers 161 to the healthcare provider 151 on a phone call. For example, a computing device 152 (used by the healthcare provider 151) may include a software application (e.g., an application, a program, etc.). The software application running on the computing device 152 (FIG. 4) allows the healthcare provider 151 to place the phone call to the user 141. The software application may allow the healthcare provider 151 to set up an account that includes a caller identification name and/or phone number that the patient 142 will recognize when the incoming call is received and displayed on the user device 142. More details regarding phone call initiation and completion are provided below. The communication server 110 can pass along information about the call to the call server 130.

In an embodiment, the call server 130 initiates the call to the carrier server 120, which will connect the phone call participants. The call server can create and send a request message that initiates the call using a signaling protocol, e.g., the Session Initiation Protocol. The call server 130 can make the call request using the information passed along by the communication server 110. Thus, the call server 130 can originate the phone call to the patient 142 through call requests sent to the carrier server 120.

The carrier server 120 can complete the call to the patient 142. The carrier server 120 can be a terminating service provider, such as a telephone company of the call recipient. The call may be communicated through additional, intermediate servers between the call server 130 and the carrier server 120 (not shown).

The carrier server 120 can be maintained by a same or different entity than that which maintains the call server 130. For example, the carrier server 120 and/or the call server 130 may be maintained by an entity that provides communication tools for making and receiving phone calls, sending and receiving text messages, and performing other communication functions. The communication functions can be performed through web service application programming interfaces, for example.

The certification authority server 135 can be controlled by an entity that provides real-time information and/or analytics for various industries, such as the telecommunications industry. For example, the certification authority server 135 can provide clearinghouse or directory services to such industries. In an embodiment, the certification authority server 135 can confirm verification and/or verify phone numbers as being associated with healthcare facilities. In response to such confirmation and/or verification, the certification authority server 135 can provide a certificate that can be checked to permit an attestation rating, e.g., an "A" attestation rating, to be applied to calls associated with the verified phone numbers.

The validation authority server 140 can be controlled by an entity that provides verification services to carriers. For example, the validation authority server 140 can communicate with the carrier server 120, as described below, to verify authenticity of calls. More particularly, the carrier server 120 can, prior to completing a call to the computing device 142 of the patient 141, request that the validation authority server 140 verify the authenticity of a certificate passed along with the call from the call server 130. In response to receiving such verification, the carrier server 120 can complete the phone call.

Processes described below may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processing device), firmware (e.g., microcode), or a combination thereof. In some embodiments, the processes may be performed by various computing devices, such as the communication server 110, the carrier server 120, the call server 130, the certification authority server 135, the validation authority server 140, etc. The actions of the patient 141 may be performed by a computing device of the patient, e.g., computing device 142, the actions of the healthcare provider 151 may be performed by a computing device of the healthcare provider, e.g., computing device 152, and the actions of the service provider 161 may be performed by a computing device of the service provider, e.g., computing device 162 (FIG. 1).

Figure 2:
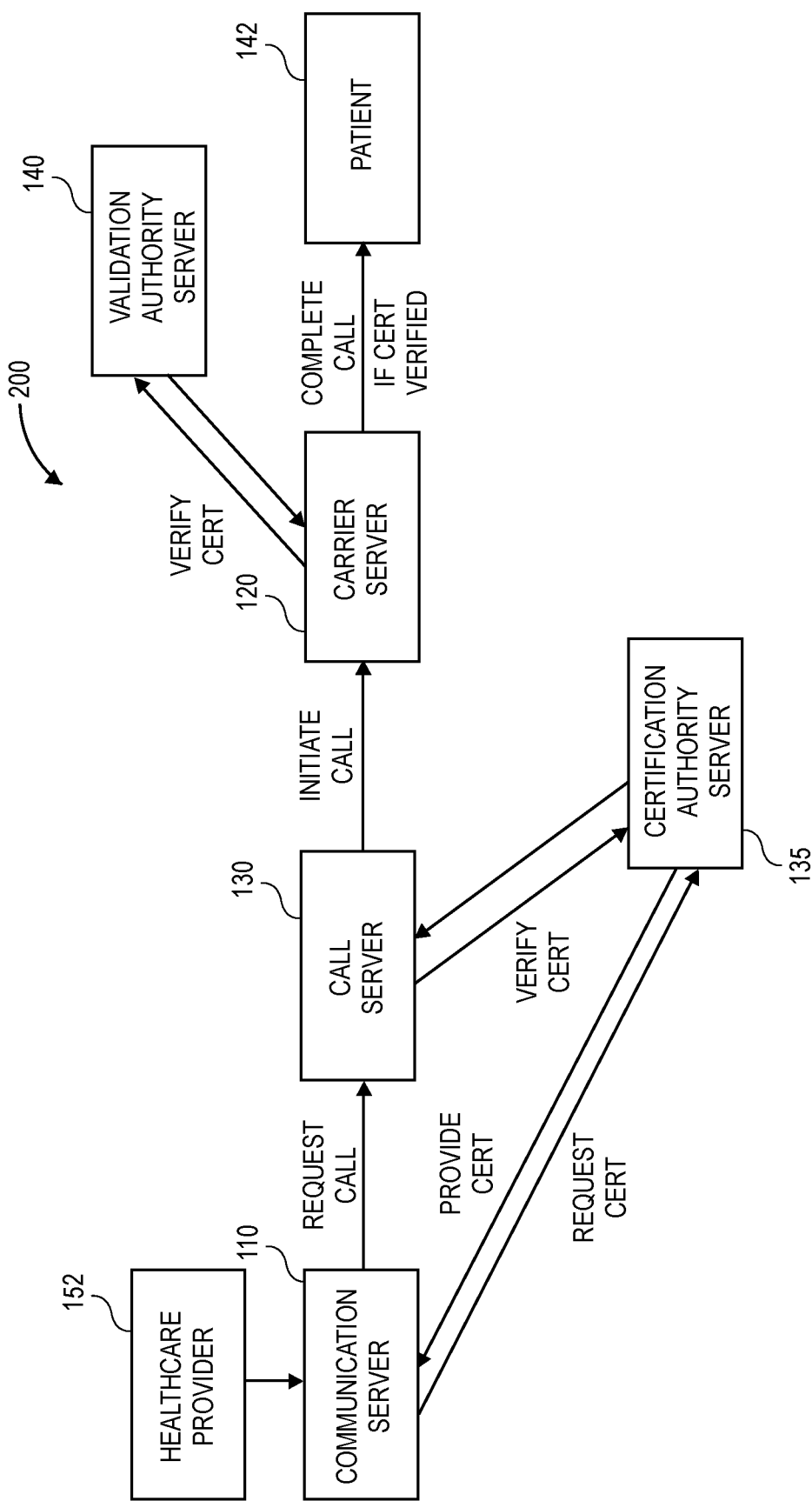
FIG. 2 is a flowchart of an example method of initiating and completing an attested phone call in accordance with one or more embodiments of the disclosure.

FIG. 2 is a flow diagram of a method of initiating and completing an attested phone call in accordance with one or more embodiments of the present disclosure. A process 200 begins when the healthcare provider 151, e.g., a doctor, uses, opens, etc., a software application (e.g., an application, software, etc.) on the computing device 152 to setup a phone call with the user 141 (e.g., a patient). The computing device 152 can receive a target phone number, e.g., a phone number of the computing device 142, and the computing device can receive a call initiation input from the healthcare provider 151, such as a selection of a "call" user interface element.

Upon selection of the call initiation input, the healthcare provider device 152 can initiate a call through the call server 130. More particularly, the call server 130 can receive the call information from the communication server 110, which may then be used to request a phone call through the call server 130. The call server 130 can communicate with the carrier server 120 to indicate that the healthcare professional 151 wants to setup a phone call with the patient 141. The carrier server 120 can originate the call to the computing device 142 of the patient. More particularly, the carrier server 120 can allow the call to pass to the computing device 142 to allow the patient 141 to answer and speak with the healthcare professional 151. Accordingly, through the network architecture described, a provider (e.g., a registered and verified healthcare professional) can initiate a call to a patient.

When originating the phone call, the call server 130 can implement STIR/SHAKEN protocols to attach a digital certificate including an attestation rating to the call information that is sent to the call recipient. More particularly, the call server 130 can attach an "A" attestation rating (full rating) to indicate that the call server 130 originated the call from a known customer (the entity operating the communication server 110) using a phone number that the known customer is known to have a right to use the phone number; or the call server 130 can attach a "B" attestation rating (partial rating) to indicate that the call server 130 originated the call from a known customer but has not verified the right of the customer to use the phone number. An "A" attestation rating can originate the call to be seen as a call from a legitimate number and a "B" or "C" attestation rating can originate the call to be seen as a potential spam call.

The call server 130 and the carrier server 120 can interact with the certification authority server 135 to attach a digital signature certifying that an outgoing call is authentic. The level of confidence in the caller's right to use the number is quantified by an attestation rating. The carrier server 120 can interact with the validation authority server 140 to verify the legitimacy of the signature when the call information is received. In an embodiment, the communication server 110 pre-verifies phone numbers and supplies pre-verification information to the certification authority server 135. As described below, the pre-verified phone numbers that are registered with the certification authority server 135 can be phone numbers associated with healthcare facilities. The entity operating the certification authority server 135 can verify the legitimacy of the phone numbers provided by the communication server 110. More particularly, the certification authority server 135 can verify that an unverified phone number is associated with a healthcare facility during a vetting process. The vetting process can include performing a secondary association of the provided caller identification information with healthcare facilities. When the vetting process successfully verified the association between the unverified phone number and the healthcare facility, the unverified phone number becomes a verified phone number. The certification authority server 135 can provide certificates for calls made from the unverified phone number (which is now a vetted and verified phone number) attesting that the phone number is being legitimately used. More particularly, the certification authority server 135 can generate such certificates for the communication server 110 as certification that the associated phone number is approved via the vetting process.

When the computing device 152 initiates the call using a phone number, the communication server 110 can request validation of the phone number from the certification authority server 135. More particularly, the communication server 110 can request that the certification authority server 135 confirm the legitimacy of the phone number. In response to such verification, the certification authority server 135 can attach a digital certificate associated with the phone number to the call. For example, the digital certificate can include a JSON Web Token, which may be requested through an application programming interface (API) of the certification authority server 135.

The communication server 110 can send a call request to the call server 130 using the validated phone number, and the call request can include the digital certificate attached by the certification authority server 135. The call server 130 can receive the digital certificate associated with the phone number, verify its authenticity, and elevate the attestation rating for the call to level "A" before initiating the call with its own digital certificate. More particularly, the digital certificate can be encoded and passed to the carrier server 120 by the call server 130 when the call server initiates the phone call.

The validation authority server 140 can certify the phone call upon request by the carrier server 120. More particularly, the carrier server 120 can request authorization of the certificate from the validation authority server 140. In response, the validation authority server 140 can verify the digital certificate received in the call request. More particularly, the validation authority server 140 can attest that the digital certificate is valid. When the validation authority server 140 authenticates the signed call request, the carrier server 120 can make a decision about how to present the phone call. The attestation rating can allow the originated call to notify the computing device 142 with a symbol, verification keyword, or alert indicating that the incoming call has been validated. Alternatively, when the validation authority server 140 does not authenticate the signed call request, the carrier server 120 may cause the originated call to be blocked by the carrier server 120 and/or to alert the computing device 142 to a potential scam call.

To ensure that phone calls placed through the call server 130 obtain a highest level of attestation possible, the communication server 110 can develop and share pre-verification information with the certification authority server 135. More particularly, given that the communication server 110 may not own the phone numbers being used to initiate the call, the communication server 110 may not ordinarily be able to prove their legitimacy in using the phone number for the call request. The method described below, however, can allow the communication server 110 to pre-verify phone numbers with the certification authority server 135 such that the certification authority server 135 can provide the digital certificate to the call server 130 after the pre-verified phone numbers are validated. To pre-verify the phone numbers, the communication server 110 can associate the phone numbers with healthcare facilities. Such pre-verification can facilitate more efficient and precise final verification of the association between the phone numbers and the healthcare facility by the certification authority server 135.

Figure 3:
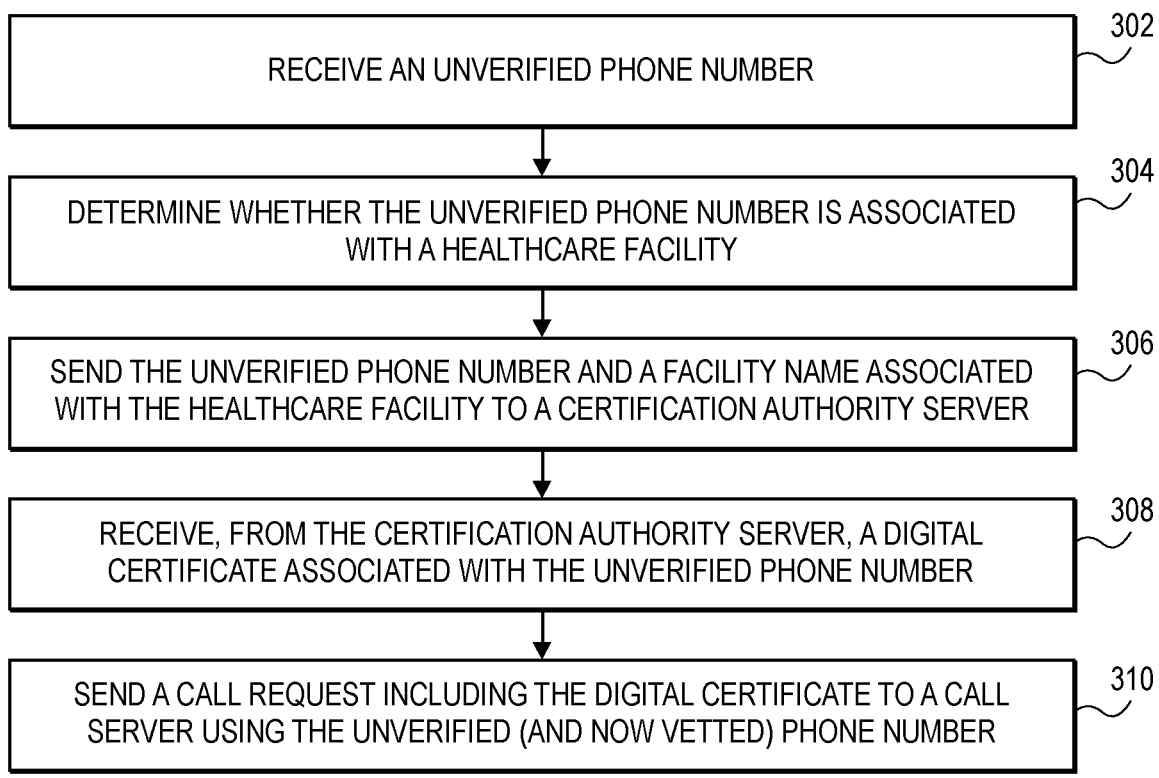
FIG. 3 is a flowchart of an example method of pre-verifying and certifying a phone number for a call request in accordance with one or more embodiments of the disclosure.

FIG. 3 is a flowchart of an example method of pre-verifying and certifying a phone number for a call request in accordance with one or more embodiments of the disclosure. The operations of the method are described with respect to FIGS. 4-5 below, and thus, FIGS. 3-5 are addressed in combination below.

Figure 4:
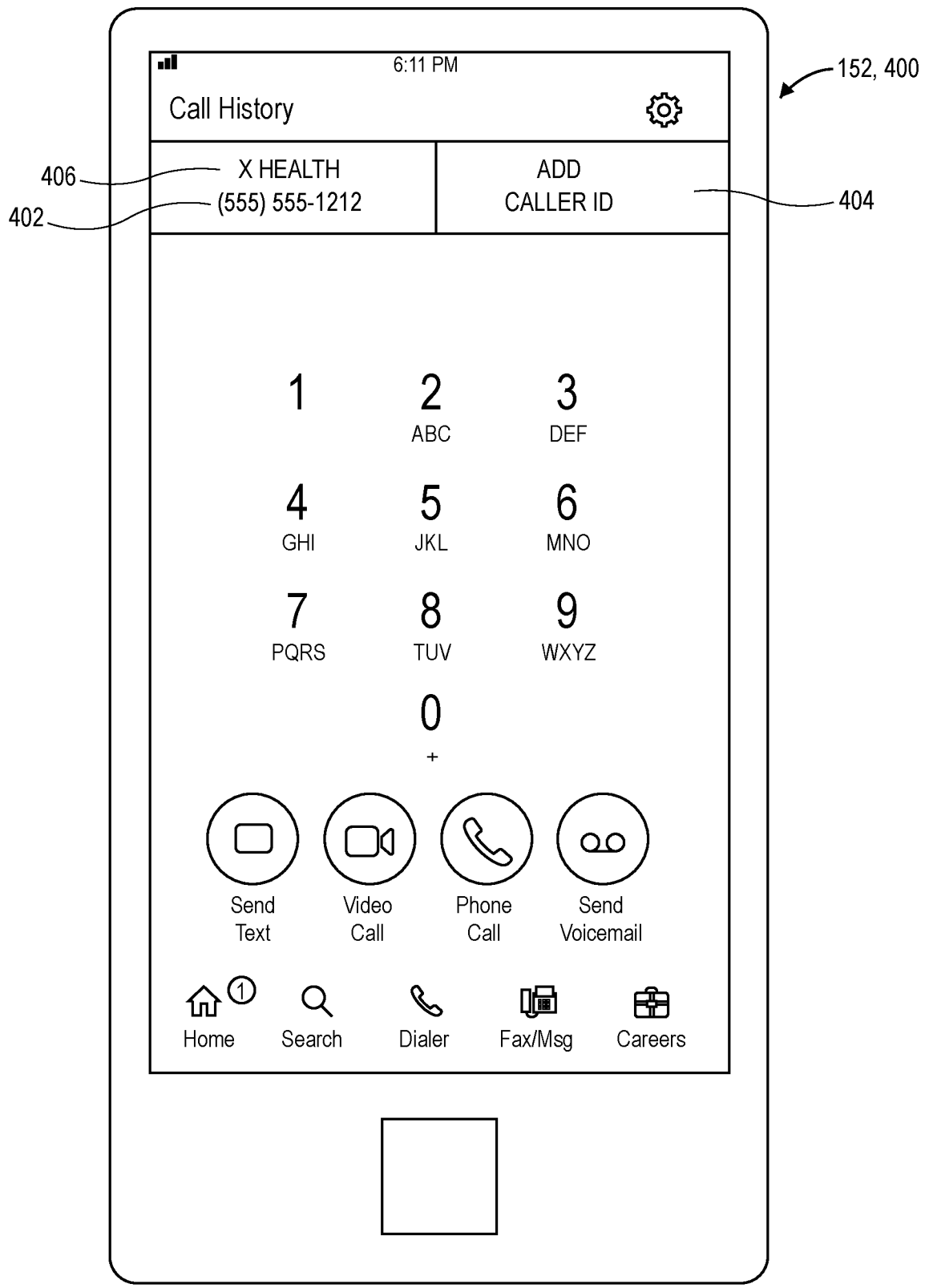
FIG. 4 is a pictorial view of a user interface in accordance with an embodiment of the disclosure.

FIG. 4 is a pictorial view of a user interface in accordance with an embodiment of the disclosure. At operation 302, the communication server 110 can receive an unverified number. The unverified number can be entered into the computing device 152, e.g., mobile device 400, before the healthcare provider 151 initiates the phone call. For example, the user of the device can select a caller identification number 402 that is different than a device phone number associated with the device. The caller identification number 402 can be configured within the software application running on the device. Alternatively, the user can select a user interface element 404 to create one or more new caller configurations. Each caller configuration can have a respective caller identification phone number 402 and a caller identification name 406. The caller identification information can be used in calls within the communication service platform provided through the communication server 110. In the example caller configuration used to initiate the phone call, the caller identification phone number ((555) 555-1212) can be associated with a corresponding caller identification name 406. In the example, the caller identification name 406 indicates a healthcare facility, e.g., "X Health." The caller identification name 406 may, however, indicate a name of the user or any other name entered by the user when the call configuration is set up. The name is for reference by the healthcare provider 151, and may not be seen on an incoming call received by the patient 142.

In an embodiment, the caller identification phone number 402 is substituted. More particularly, given that the caller identification phone number 402 from which the call is initiated differs from the device phone number, the phone number is substituted. Nonetheless, the phone number may be legitimately substituted by a healthcare provider, and thus, the communication server 110 may coordinate with the certification authority server 135 to ensure that the unverified phone number is properly associated with the healthcare facility for certification. Such certification can facilitate an "A" attestation of a phone call initiated from the legitimately substituted phone number.

Figure 5:
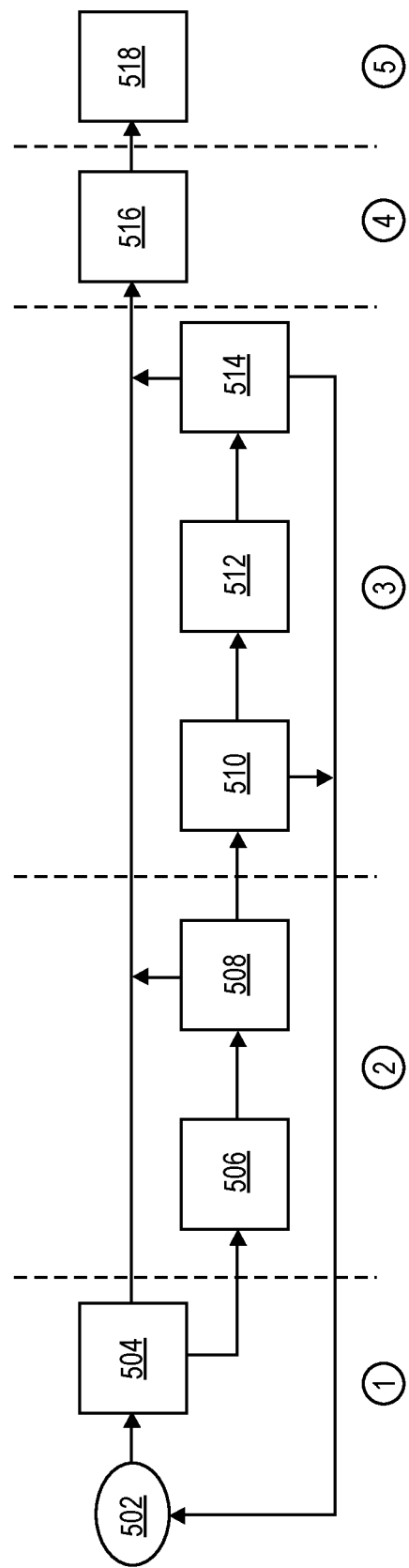
FIG. 5 is a flowchart of an example method of pre-verifying a phone number for a call request in accordance with one or more embodiments of the disclosure.

FIG. 5 is a flowchart of an example method of pre-verifying a phone number for a call request in accordance with one or more embodiments of the disclosure. At operation 304, the communication server 110 can determine whether the unverified phone number is associated with a healthcare facility. Pre-verification of the caller identification information, e.g., the caller identification phone number, can include associating the phone number with a healthcare facility. At block 502, the unverified phone number, which may be the caller identification phone number 402, is obtained. As discussed above, the unverified phone number may be received when the healthcare provider initiates the phone call. Alternatively, the communication server 110 can obtain the unverified phone number prior to the call initiation. For example, as users configure and/or set up profiles having corresponding caller identification names 406 and phone numbers 402 through the software application running on various devices, the devices can communicate the profile information to the communication server 110. The communication server 110 can obtain caller configuration information, including the phone numbers that are unverified numbers at that time, and perform one or more techniques to determine whether the unverified number is associated with a healthcare facility. Such techniques can use sources of data available to the communication server 110 to link the unverified phone number to a known medical facility. The techniques are described in more detail below.

In a first phase, at block 504, the communication server 110 can match phone numbers to a data source, such as an internal facility directory, to determine whether the unverified phone numbers are associated with a healthcare facility. More particularly, determining whether the unverified phone number is associated with the healthcare facility can include matching the unverified phone number to a facility phone number associated with the healthcare facility. This technique, which may be referred to as direct facility matching, may include determining whether the unverified phone number is a primary number of the healthcare facility. The communication server 110 can include an internal facility listing having a listing of healthcare facilities and the primary phone numbers of those facilities. The primary phone number may be found attached to an entry in the internal facility listing for a particular healthcare facility. In such case, the communication server 110 can determine directly that the unverified number is a legitimately substituted caller identification phone number corresponding to the healthcare facility. More particularly, the fact that the unverified number can be found in an internal database of the communication server 110 linked to a verified healthcare facility can give confidence that the unverified number is a facility phone number associated with the healthcare facility.

In the event that the unverified number fails to be verified as belonging to a healthcare facility in the first phase, the method can progress to a second phase at block 506. At block 506, information can be retrieved from the call server 130. The information can be retrieved through an API that allows for a business information lookup to be performed on databases of the call server 130. More particularly, the communication server 110 can use the API to retrieve metadata from the call server 130. The metadata can include business and address information. For example, the metadata can include, for a given phone number, a business name, a business identifier, a business address, etc. When the unverified number corresponds to a healthcare facility, performing the lookup through the API using the unverified phone number can result in retrieval of a facility name, a national provider identifier (NPI), a facility address, etc., corresponding to the unverified phone number. The second phase can involve matching data stored internally at the communication server 110 to data stored externally at the call server 130. Several matching techniques can be used to perform this matching between the information stored by the communication server 110 and the call server 130. At block 508, the information retrieved from the communication server 110 can be analyzed to match information corresponding to the unverified phone number in the call server 130 to a healthcare facility corresponding to the same information in the communication server 110. Such a match links the healthcare facility to the unverified phone number, and provides pre-verification of the unverified phone number as being associated with the healthcare facility. Matching between communication server information and call server information can be performed using several techniques, as described below.

The communication server 110 can determine whether the unverified phone number is associated with the healthcare facility using a raw matching technique. The raw matching technique can match national provider identifier (NPI) information between call server and communication server databases to infer an association between the unverified phone number and a healthcare facility. In an embodiment, the communication server 110 can request and receive, e.g., retrieve, the NPI information from the carrier server 120. For example, the communication server 110 can submit the unverified phone number and retrieve the corresponding NPI information through the API of the carrier server 120. The NPI information retrieved from the carrier server 120 can be matched to NPI information stored in a database of the communication server 110. The communication server 110 may also maintain a directory of the NPI entities, which includes healthcare facilities and their corresponding NPI numbers, phone numbers, addresses, etc. In an embodiment, when a first national provider identifier associated with the unverified number in a first database of the carrier server 120 matches a second national provider identifier associated with a healthcare facility in a second database of the communication server 110, the unverified number may be determined to correspond to the healthcare facility. Accordingly, although the unverified phone number may not be directly stored in a database of the communication server 110, the fact that the unverified phone number is linked to an NPI number in a database of the carrier server 120 allows the inference that the unverified phone number is also associated with the same NPI number found in the call server database. More particularly, by linking the NPI number to the healthcare facility, the communication server 110 can determine that the unverified phone number is associated with the healthcare facility.

The indirect raw matching technique can also be used to infer an association between the unverified phone number and the healthcare facility based on other indirect matching information. For example, the communication server 110 can retrieve the information through the API of the carrier server 120, and the information can include facility address information. The facility address information retrieved from the call server 130 can be matched to facility address information stored in a database of the communication server 110. The directory of healthcare facilities maintained at the communication server 110 can include healthcare facilities and their corresponding addresses. In an embodiment, when a first facility address associated with the unverified number in a first database of the call server 130 matches a second facility address associated with the healthcare facility in a second database of the communication server 110, the unverified number may be determined to correspond to the healthcare facility. Accordingly, although the unverified phone number may not be directly stored in a database of the communication server 110, the fact that the unverified phone number is linked to a facility address in a database of the call server 130 allows the inference that the unverified phone number is also associated with the same facility address found in the call server database. More particularly, by linking the address to the healthcare facility, the communication server 110 can determine that the unverified phone number is associated with the healthcare facility.

The communication server 110 can determine whether the unverified phone number is associated with the healthcare facility using a fuzzy matching technique. The fuzzy matching technique can include one or more indirect matching techniques to determine that the unverified phone number, which is not directly matched within an internal database of the communication server 110, is associated with the healthcare facility.

In an embodiment, a fuzzy matching technique includes determining whether the unverified phone number partially matches a facility phone number associated with a healthcare facility. More particularly, one or more of the digits in the unverified phone number can be compared to number sequences in the facility phone numbers stored in the internal database of the call server 130. In an embodiment, the initial 6 digits of the caller identification phone number 402 are selected for matching. For example, in the caller identification phone number 402 of FIG. 4, the initial digits "555 555" can be selected for comparison to phone numbers in the internal listing. If those digits match the initial 6 digits of a listed phone number, then the unverified phone number can be determined to be associated with the healthcare facility corresponding to the listed phone number.

Rather than generating a determination between the unverified phone number and the listed phone number, the partial match may be one of several criteria that must be met to determine a match. For example, another criteria may be a predetermined similarity between a caller identification name 406 associated with the unverified phone number and a facility name listed in the internal database. In an embodiment, the similarity is determined based on a Levenshtein distance between the names. A Levenshtein distance is a string metric for determining, e.g., measuring, the difference between two sequences, such as between two names. The communication server 110 can determine whether a Levenshtein distance between a caller identification name 406 associated with the unverified phone number and a facility name associated a healthcare facility is above a predetermined threshold, e.g., 50%. In the example of FIG. 4, the caller identification name 406 is shown as "X Health." The internal database may list a healthcare facility named "X Healthcare." Using the fuzzy matching technique, a Levenshtein distance between "X Health" and "X Healthcare" may have a value above the predetermined value. Accordingly, the unverified phone number associated with the caller identification name "X Health" can be determined to be associated with the healthcare facility "X Healthcare."

Alternatively or additionally, another criteria for determining the association between the unverified phone number and the healthcare facility may include a direct comparison of caller identification names. More particularly, one or more processing devices of the communication server 110 can determine whether the facility name associated with the healthcare facility includes the caller identification name associated with the unverified phone number. For example, the caller identification name may be completely contained within the healthcare facility name stored in the internal database. In the example above, the facility name "X Healthcare" completely contains the caller identification name "X Health" because all of the alphanumeric characters of "X Health" are found in the same sequence within "X Healthcare." Accordingly, the unverified phone number associated with the caller identification name "X Health" can be determined to be associated with the healthcare facility "X Healthcare."

The fuzzy matching techniques described above may be used independently, or as criteria in pre-verifying the unverified phone number. For example, the partial matching of names may be combined with the Levenshtein distance measurement in an AND logic determination. Alternatively, a positive determination of association between the unverified phone number and the facility name may be made if only one of the fuzzy matching criteria is met. Thus, the criteria may be combined in an OR logic determination to conclude that the unverified phone number is associated with the healthcare facility.

In the event that the unverified phone number fails to be verified as belonging to a healthcare facility in the second phase, the method can progress to a third phase at block 510. The third phase can provide an external number match. In the external number match, the unverified phone number may be sent to a third party to be manually reviewed. Information resulting from the manual review can include the phone number, address, and business name of a healthcare facility associated with the unverified number. More particularly, the third party can research various data sources to find a match between phone numbers in the data sources and the unverified phone number. When a match is determined, the third party can send the information to the communication server 110. At block 512, the communication server 110 can load the external number match information for further analysis. More particularly, at block 514, the communication server 110 can match the external number match information to information previously stored at the communication service 110. For example, caller identification names 406, addresses, or other information associated with the unverified phone number in the external data sources can be matched to entries within the call server databases. If a match, e.g., between an address in the external data source information and the internal database information, exists, a healthcare facility corresponding to the matching internal data entry can be determined to correspond to the unverified phone number.

In a fourth phase, if any of blocks 504, 508, or 514 result in a determination that the unverified phone number is associated with the healthcare facility, the method can progress to block 516 at which the communication server 110 can generate pre-verification information to send to the certification authority server 135. The pre-verification information can be stored in a file, such as a comma-separated values (CSV) file, that includes the unverified phone number and a facility name associate with the healthcare facility. The CSV file can include entries for one or more healthcare facilities that the communication server 110 has matched to corresponding unverified phone numbers. At this stage, the unverified phone numbers may more aptly be referred to as pre-verified phone numbers, given that the communication server 110 has pre-verified the phone numbers as legitimately substituted numbers corresponding to legitimate healthcare facilities.

At operation 306 (FIG. 3), and in a fifth stage at block 518 (FIG. 5), the communication server 110 can send the pre-verification information to the certification authority server 135. More particularly, the communication server 110 can submit the pre-verification information to the certification authority server 135 for vetting. The pre-verification information, which includes the unverified phone number and the facility name, may be received and validated by the entity maintaining the certification authority server 135. For example, the entity can perform internal matching of the information during a vetting process to confirm that the unverified (pre-verified) phone number is associated with the healthcare facility, and thus, a legitimately substituted phone number. In response to such determination, the certification authority server 135 can attach a digital certificate to the call metadata attesting to the phone number being authorized to have an "A" attestation level when queried by the call server 130.

At operation 308, during the call placement shown in FIG. 2, the communication server 110 can request certification of the unverified phone number when the call is placed. The communication server 110 can receive, from the certification authority server 135, a digital certificate associated with the unverified phone number. Such digital certificate can be provided upon completion of the verification of the pre-verified information as described above.

The digital certificate received by the communication server 110 from the certification authority server 135 can be used by the communication server 110 to request the phone call from the call server 130. More particularly, at operation 310, the communication server 110 can send a call request including the digital certificate to the call server 130. The call request can use the unverified phone number, which at this stage has been vetted by the certification authority server 135, in making the request. Accordingly, the call request can provide the digital certificate for the now verified number to the call server 130.

The call server 130 can respond to the request for the call from the communication server 110 by checking with the certification authority server 135, as described above. More particularly, the call server 130 can check with the certification authority server 135 to verify certification of the phone number associated with the call. When the call server 130 receives authorization from the certification authority server 135, the call server 130 can attach the appropriate attestation rating, e.g., an "A" rating, and originate the call to the computing device 142.

Figure 6:
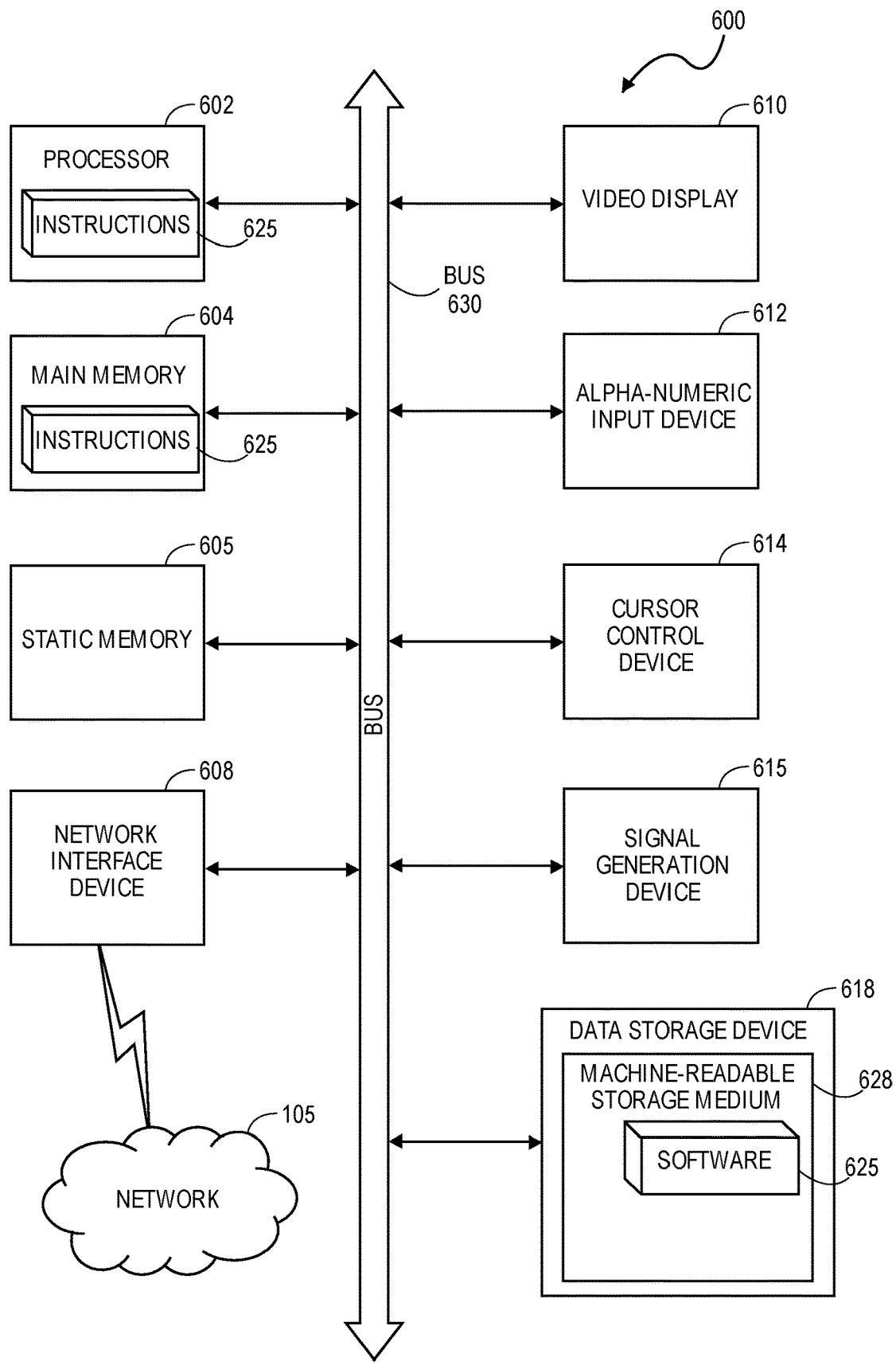
FIG. 6 is a block diagram of an example computing device that may perform one or more of the operations described herein, in accordance with some embodiments.

FIG. 6 is a block diagram of an example computing device that may perform one or more of the operations described herein, in accordance with some embodiments. More particularly, computing device 600 may be integrated in any of the servers and/or devices described above to perform any of the described operations. Computing device 600 may be connected to other computing devices in a LAN, an intranet, an extranet, and/or the Internet. The computing device may operate in the capacity of a server machine in the client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 600 may include one or more processing devices (e.g., a processing device, a general purpose processing device, a PLD, etc.) 602, a main memory 604 (e.g., synchronous dynamic random access memory (DRAM), read-only memory (ROM)), a static memory 605 (e.g., flash memory and a data storage device 618), which may communicate with each other via a bus 630.

The one or more processing devices 602 may be provided by one or more general-purpose processing devices such as a microprocessor, central processing unit, or the like. In an illustrative example, processing device(s) 602 may comprise a complex instruction set computing (CISC) microprocessor, reduced instruction set computing (RISC) microprocessor, very long instruction word (VLIW) microprocessor, or a processing device implementing other instruction sets or processing devices implementing a combination of instruction sets. Processing device(s) 602 may also comprise one or more special-purpose processing devices such as an application specific integrated circuit (ASIC), a field programmable gate array (FPGA), a digital signal processor (DSP), network processor, or the like. The processing device(s) 602 may be configured to execute the operations described herein, in accordance with one or more aspects of the present disclosure, for performing the operations and steps discussed herein.

Computing device 600 may further include a network interface device 608 which may communicate with a network 105. The computing device 600 also may include a video display unit 610 (e.g., a liquid crystal display (LCD) or a cathode ray tube (CRT)), an alphanumeric input device 612 (e.g., a keyboard), a cursor control device 614 (e.g., a mouse) and an acoustic signal generation device 615 (e.g., a speaker). In one embodiment, video display unit 610, alphanumeric input device 612, and cursor control device 614 may be combined into a single component or device (e.g., an LCD touch screen).

Data storage device 618 may include a computer-readable storage medium 628 on which may be stored one or more sets of instructions 625 that may include instructions for carrying out the operations described herein, in accordance with one or more aspects of the present disclosure. Instructions 625 may also reside, completely or at least partially, within main memory 604 and/or within processing device(s) 602 during execution thereof by computing device 600, main memory 604 and processing device(s) 602 also constituting computer-readable media. The instructions 625 may further be transmitted or received over a network 620 via network interface device 608.

While computer-readable storage medium 628 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A method, comprising:
   receiving, by one or more processing devices of a communication server, an unverified phone number;
   generating, by the one or more processing devices, pre-verification information, in response to determining the unverified phone number is associated with a healthcare facility, wherein the pre-verification information includes the unverified phone number and a facility name associated with the healthcare facility;
   sending, by the one or more processing devices, the pre-verification information to a certification authority server for use in verifying that the unverified phone number is associated with the healthcare facility; and
   sending, by the one or more processing devices, a call request using the unverified phone number, wherein the call request includes a digital certificate based on the certification authority server verifying that the unverified phone number is associated with the healthcare facility.

2. The method of claim 1, wherein the unverified phone number is a caller identification phone number configured on a device, and wherein the caller identification phone number is different than a device phone number associated with the device.

3. The method of claim 1, wherein determining whether the unverified phone number is associated with the healthcare facility includes matching the unverified phone number to a facility phone number associated with the healthcare facility.

4. The method of claim 1, wherein determining whether the unverified phone number is associated with the healthcare facility includes determining whether the unverified phone number partially matches a facility phone number associated with the healthcare facility.

5. The method of claim 4, wherein determining whether the unverified phone number is associated with the healthcare facility includes determining whether a Levenshtein distance between a caller identification name associated with the unverified phone number and the facility name associated with the healthcare facility is above a predetermined threshold.

6. The method of claim 1, wherein determining whether the unverified phone number is associated with the healthcare facility includes determining whether the facility name associated with the healthcare facility includes a caller identification name associated with the unverified phone number.

7. The method of claim 1, wherein determining whether the unverified phone number is associated with the healthcare facility includes matching a first national provider identifier associated with the unverified phone number in a first database to a second national provider identifier associated with the healthcare facility in a second database.

8. The method of claim 1, wherein determining whether the unverified phone number is associated with the healthcare facility includes matching a first facility address associated with the unverified phone number in a first database to a second facility address associated with the healthcare facility in a second database.

9. The method of claim 1 further comprising
   receiving, in response to the verification by the certification authority server, the digital certificate associated with the unverified phone number.

10. The method of claim 9 further comprising sending the call request to a carrier server using the unverified phone number.

11. A system comprising:
    a memory storing an unverified phone number; and
    one or more processing devices configured to:
      generate pre-verification information, in response to determining the unverified phone number is associated with a healthcare facility, wherein the pre-verification information includes the unverified phone number and a facility name associated with the healthcare facility,
      send the pre-verification information to a certification authority server for use in verifying that the unverified phone number is associated with the healthcare facility, and
      send a call request using the unverified phone number, wherein the call request includes a digital certificate based on the certification authority server verifying that the unverified phone number is associated with the healthcare facility.

12. The system of claim 11, wherein the unverified phone number is a caller identification phone number configured on a device, and wherein the caller identification phone number is different than a device phone number associated with the device.

13. The system of claim 11, wherein determining whether the unverified phone number is associated with the healthcare facility includes matching the unverified phone number to a facility phone number associated with the healthcare facility.

14. The system of claim 11, wherein determining whether the unverified phone number is associated with the healthcare facility includes determining whether the unverified phone number partially matches a facility phone number associated with the healthcare facility, and determining whether a Levenshtein distance between a caller identification name associated with the unverified phone number and the facility name associated with the healthcare facility is above a predetermined threshold.

15. The system of claim 11, wherein determining whether the unverified phone number is associated with the healthcare facility includes determining whether the facility name associated with the healthcare facility includes a caller identification name associated with the unverified phone number.

16. A non-transitory computer readable storage medium storing instructions executable by one or more processing devices of a system to cause the system to perform a method comprising:
  receiving, by the one or more processing devices, an unverified phone number;
  generating, by the one or more processing devices, pre-verification information, in response to determining whether the unverified phone number is associated with a healthcare facility, wherein the pre-verification information includes the unverified phone number and a facility name associated with the healthcare facility; and
  sending, by the one or more processing devices, the pre-verification information to a certification authority server for use in verifying that the unverified phone number is associated with the healthcare facility; and
  sending, by the one or more processing devices, a call request using the unverified phone number, wherein the call request includes a digital certificate based on the certification authority server verifying that the unverified phone number is associated with the healthcare facility.

17. The non-transitory computer readable storage medium of claim 16, wherein the unverified phone number is a caller identification phone number configured on a device, and wherein the caller identification phone number is different than a device phone number associated with the device.

18. The non-transitory computer readable storage medium of claim 16, wherein determining whether the unverified phone number is associated with the healthcare facility includes matching the unverified phone number to a facility phone number associated with the healthcare facility.

19. The non-transitory computer readable storage medium of claim 16, wherein determining whether the unverified phone number is associated with the healthcare facility includes determining whether the unverified phone number partially matches a facility phone number associated with the healthcare facility, and determining whether a Levenshtein distance between a caller identification name associated with the unverified phone number and the facility name associated with the healthcare facility is above a predetermined threshold.

20. The non-transitory computer readable storage medium of claim 16, wherein determining whether the unverified phone number is associated with the healthcare facility includes determining whether the facility name associated with the healthcare facility includes a caller identification name associated with the unverified phone number.

* * * * *